(12) United States Patent
Padmanabhan et al.

(10) Patent No.: US 7,671,987 B2
(45) Date of Patent: *Mar. 2, 2010

(54) OPTICAL DETECTION SYSTEM FOR FLOW CYTOMETRY

(75) Inventors: Aravind Padmanabhan, Plymouth, MN (US); Bernard S. Fritz, Eagan, MN (US)

(73) Assignee: Honeywell International Inc, Morristown, NJ (US)

( * ) Notice: Subject to any disclaimer, the term of this patent is extended or adjusted under 35 U.S.C. 154(b) by 823 days.

This patent is subject to a terminal disclaimer.

(21) Appl. No.: 11/030,407

(22) Filed: Jan. 6, 2005

(65) Prior Publication Data

US 2005/0122522 A1    Jun. 9, 2005

Related U.S. Application Data

(63) Continuation-in-part of application No. 10/304,773, filed on Nov. 26, 2002, which is a continuation-in-part of application No. 09/630,924, filed on Aug. 2, 2000, now Pat. No. 6,597,438, application No. 11/030,407, which is a continuation-in-part of application No. 10/225,325, filed on Aug. 21, 2002, now Pat. No. 6,970,245, which is a continuation-in-part of application No. 09/630,927, filed on Aug. 2, 2000, now Pat. No. 6,549,275.

(51) Int. Cl.
 *G01B 11/00* (2006.01)
(52) U.S. Cl. .................................. 356/338; 356/341
(58) Field of Classification Search ................ 356/337, 356/338
See application file for complete search history.

(56) References Cited

U.S. PATENT DOCUMENTS

| 3,822,095 | A |   | 7/1974  | Hirschfeld |
|-----------|---|---|---------|------------|
| 3,928,094 | A |   | 12/1975 | Angell |
| 3,976,862 | A |   | 8/1976  | Curbelo |
| 4,284,412 | A |   | 8/1981  | Hansen et al. |
| 4,385,834 | A | * | 5/1983  | Maxwell, Jr. ............... 356/153 |
| 4,478,076 | A |   | 10/1984 | Bohrer |
| 4,478,077 | A |   | 10/1984 | Boher |
| 4,501,144 | A |   | 2/1985  | Higashi et al. |

(Continued)

FOREIGN PATENT DOCUMENTS

DE    10122321    4/2002

(Continued)

OTHER PUBLICATIONS http://www.micronics.net/tsensor.htm, pp. 1-4, downloaded Jun. 14, 2000.

(Continued)

*Primary Examiner*—Gregory J Toatley, Jr.
*Assistant Examiner*—Rebecca C Slomski
(74) *Attorney, Agent, or Firm*—Kris T. Fredrick

(57) ABSTRACT

An optical detection system for flow cytometry that uses light sources positioned laterally at different distances from the central axis of the flow stream for providing light through different parts of the flow stream. By using two or more light sources, the particle position can be detected, and the alignment and width of the core stream can be monitored and controlled.

22 Claims, 13 Drawing Sheets

U.S. PATENT DOCUMENTS

| | | | |
|---|---|---|---|
| 4,573,796 A * | 3/1986 | Martin et al. | 356/318 |
| 4,599,000 A | 7/1986 | Yasuyoshi | |
| 4,651,564 A | 3/1987 | Johnson et al. | |
| 4,683,159 A | 7/1987 | Bohrer et al. | |
| 4,695,034 A | 9/1987 | Shimizu et al. | |
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,911,616 A | 3/1990 | Laumann, Jr. | |
| 4,932,989 A | 6/1990 | Presby | |
| 5,017,497 A | 5/1991 | de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,591,981 A * | 1/1997 | Heffelfinger et al. | 250/458.1 |
| 5,601,080 A | 2/1997 | Oppenheimer | |
| 5,616,501 A | 4/1997 | Rodriguez | |
| 5,633,724 A | 5/1997 | King et al. | |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerie et al. | |
| 6,116,756 A | 9/2000 | Peeters et al. | |
| 6,124,663 A | 9/2000 | Haake et al. | |
| 6,139,800 A * | 10/2000 | Chandler | 422/82.08 |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 | 5/2002 | Cabuz et al. | |
| 6,407,812 B1 * | 6/2002 | Kurozumi et al. | 356/336 |
| 6,549,275 B1 | 4/2003 | Cabuz et al. | |
| 6,573,991 B1 * | 6/2003 | Debreczeny et al. | 356/336 |
| 6,597,438 B1 | 7/2003 | Cabuz et al. | |
| 6,710,870 B1 * | 3/2004 | Marowsky et al. | 356/317 |
| 7,012,689 B2 * | 3/2006 | Sharpe | 356/399 |
| 2003/0142291 A1 | 7/2003 | Padmanabhan et al. | |
| 2006/0152721 A1 * | 7/2006 | Korkeamaki et al. | 356/318 |

FOREIGN PATENT DOCUMENTS

| | | |
|---|---|---|
| EP | 0269076 | 6/1988 |
| EP | 1001326 | 5/1999 |
| EP | 1134548 | 9/2001 |
| JP | 61066947 | 4/1986 |
| JP | 10073528 | 8/1996 |
| JP | 2000056228 | 7/1999 |
| WO | WO 95/27199 | 3/1995 |
| WO | WO 99/60397 | 4/1999 |
| WO | WO 01/09598 | 7/2000 |
| WO | WO 02/10713 A2 | 2/2002 |
| WO | WO 02/10713 A3 | 2/2002 |
| WO | WO 02/10714 | 2/2002 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using A Prototype Microfluidics-Based Hematology Analyzer", SPIE Biomedical Optics 97, 1997.

Altendorf et al., "Differential Blood Cell Counts Obtained Using A Microchannel Based Flow Cytometer", Solid State Sensors & Actuators, vol. 1, 531, 1997.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Microfabrication Technology For Research And Diagnostics, Silicon Microchannel Optical FLow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers '99, Jun. 7-12, 1999, Sendai Japan, p. 1890-1.

Darling et al., "Integration Of Microelectrodes With Etched Microchannels For In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches To Immunoassays", SPIE conference on Micromachining and Microfabrication Symposium at Santa Clara, CA, Sep. 20-22, 1999.

Huang et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3$^{rd}$ International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/ Sheraton Kauai Resort, Kauai, Hawaii, Aug. 21-24, 2000, 2 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Weigh et al, "Silicon-Microfabricated Diffusion-Based Optical Chemical Sensor", Reprint from "Sensors & Actuators" B 38-39, 452-457, 1997.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, µTTAS 96 special edition, 1996.

Wiegl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", µTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

* cited by examiner

OPTICAL DETECTION SYSTEM FOR FLOW CYTOMETRY

The present patent application also claims priority as a continuation-in-part of U.S. Nonprovisional Patent Application Ser. No. 10/304,773, filed Nov. 26, 2002, and entitled "Portable Scattering and Fluorescence Cytometer", which is a continuation-in-part of U.S. Nonprovisional Patent Application Ser. No. 09/630,924, filed Aug. 2, 2000 now U.S. Pat. No. 6,597,438, and entitled "Portable Flow Cytometer", both of which are incorporated herein by reference.

The present patent application also claims priority as a continuation-in-part of U.S. Nonprovisional Patent Application Ser. No. 10/225,325, filed Aug. 21, 2002 now U.S. Pat. No. 6,970,245, and entitled "Optical Alignment Detection System", which is a continuation-in-part of U.S. Nonprovisional Patent Application Ser. No. 09/630,927, filed Aug. 2, 2000 now U.S. Pat. No. 6,549,275, and entitled "Optical Detection System For Flow Cytometery", both of which are incorporated herein by reference.

BACKGROUND

The present invention relates generally to flow cytometers, and more particularly to portable flow cytometers that sense optical properties of microscopic biological particles or components in a flow stream.

Flow cytometry is a technique that is used to determine certain physical and chemical properties of microscopic biological particles or components by sensing certain optical properties of the particles or components. To do so, for instance, the particles are arranged in single file using hydrodynamic focusing within a sheath fluid. The particles are then individually interrogated by a light beam. Each particle scatters the light beam and produces a scatter profile. The scatter profile is often identified by measuring the light intensity at different scatter angles. Certain physical and/or chemical properties of each particle can then be determined from the scatter profile.

Flow cytometry is currently used in a wide variety of applications including hematology, immunology, genetics, food science, pharmacology, microbiology, parasitology and oncology, to name a few. A limitation of many commercially available flow cytometer systems is that they are relatively large bench top instruments that must remain in a central laboratory environment. Accordingly, the use of such flow cytometers is often not available in remote locations or for continuous hematological monitoring.

SUMMARY

The present invention overcomes many of the disadvantages of the prior art by providing an optical detection system that uses two or more light sources positioned laterally at different distances from the central axis of the flow stream for providing light through different parts of the flow stream. By using two or more light sources, the particle position can be detected, and the alignment and width of the core stream can be monitored and controlled. In addition, the velocity and size of the particles can be more accurately determined than in single light source systems.

In one illustrative embodiment of the present invention, a linear array of first light sources that extend along a first light source axis are provided. The first light source axis is rotated relative to the central axis of the flow stream. A lens is provided adjacent each light source to focus the light at the particles in the core stream. A first set of light detectors are placed in-line with each of the first light sources.

Such an arrangement can be used to determine, for example, the lateral position of each of the particles in the core stream, and the alignment and width of the core stream within the overall flow stream. If the core stream of particles has an improper width or is not in proper alignment, a controller can be used to adjust the fluid velocity of the sample fluid or one of the supporting fluids to adjust the width of the core stream or bring the core stream into alignment. The first set of light detectors may also be used to detect the time-of-flight or velocity of each particle, the size of each particle, as well as the number of particles that flow by the detector.

A second set of the light sources may also be provided along a second light source axis. A lens may be provided adjacent each light source to focus the light at the particles in the core stream. A second set of light detectors may then be placed on either side of the in-line position of each light source for measuring the small angle scattering (SALS) produced by selected particles in the flow stream. The second set of light sources may also be used in conjunction with the first set of light sources to determine the time-of-flight or velocity of the particles in the flow stream. By knowing the velocity of the particles, small variations in the flow rate caused by the fluid driver can be minimized or removed by the controller.

A third set of light sources may be provided along a third light source axis. A lens may be provided adjacent each light source to provide collimated light to the flow stream. Annular light detectors may then be placed opposite the light sources for measuring the forward angle scattering (FALS) produced by the selected particles in the flow stream.

The optical detection system of the present invention may be used in conjunction with a portable cytometer system for detecting, for example, neutrophils and/or lymphocytes white blood cells in a blood sample. By examining the scatter profile of each of the particles, the portable cytometer may identify and count the neutrophils and lymphocytes in the blood sample, and provide a clear infection warning with differentiation between viral and bacterial causes.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION

Figure 1:
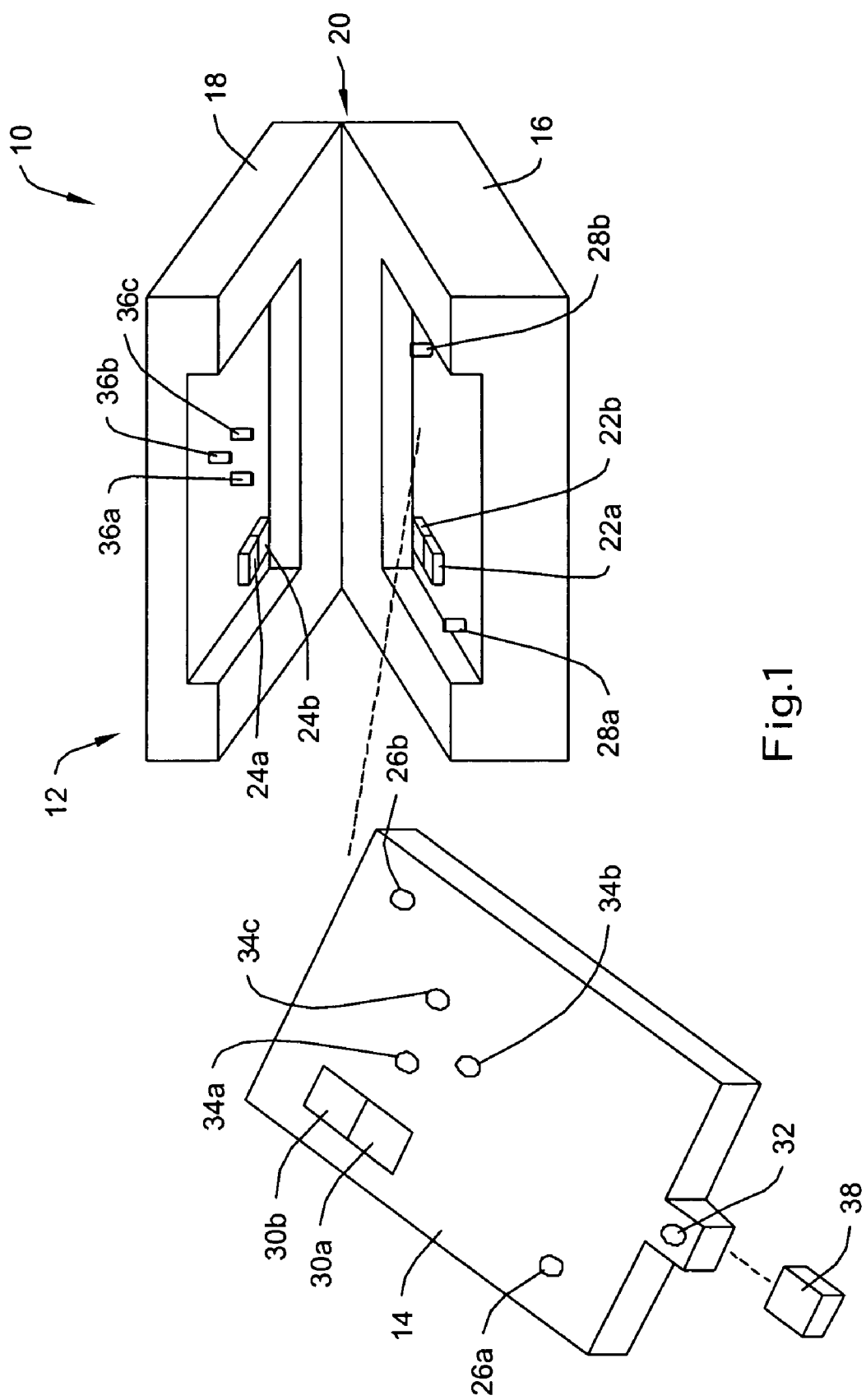
FIG. 1 is a perspective view of an illustrative portable cytometer in accordance with the present invention.

FIG. 1 is a perspective view of an illustrative miniaturized portable cytometer in accordance with the present invention. The cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes light sources 22a and 22b, associated optics and the necessary electronics for operation of the cytometer. The cover 12 includes a manual pressurizing element, pressure-chambers with control microvalves, and light detectors 24a and 24b with associated optics.

The removable cartridge 14 may receive a sample fluid via a sample collector port 32. A cap 38 may be used to protect the sample collector port 32 when the removable cartridge 14 is not in use. The removable cartridge 14 may perform blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable structure or cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also may include transparent flow stream windows 30a and 30b, which are in alignment with the arrays of the light sources 22a and 22b, and light detectors 24a and 24b. In some cases, an actuator (not explicitly shown) may be provided to help align the removable cartridge 14 relative to the housing 12, and/or to move a lens such as lens 220 of FIG. 10 to steer the beam from the light source. The actuator may be controlled, at least in part, by a controller or processor 40 (see FIG. 2).

In the illustrative embodiment, when the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22a and 22b, light detectors 24a and 24b and associated control and processing electronics perform differentiation and counting of white blood cells based on light scattering fluorescent signals. Rather than using a hinged construction for the housing 12, it is contemplated that a sliding cartridge slot or any other suitable construction may be used.

Figure 2:
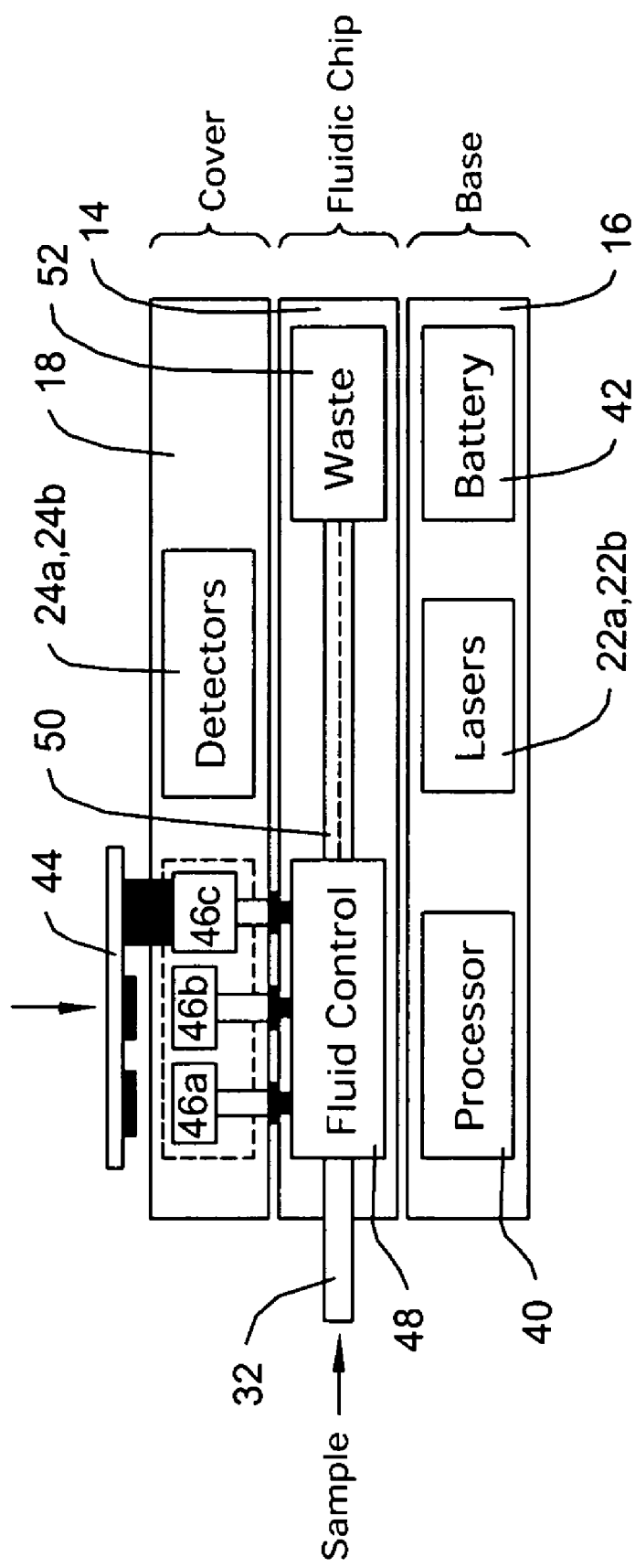
FIG. 2 is a schematic view of the illustrative portable cytometer of FIG. 1.

FIG. 2 is a schematic view of the illustrative cytometer of FIG. 1. As above, the base 16 may include light sources 22a and 22b, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and light detectors 24a and 24b with associated optics.

The removable cartridge 14 may receive a sample fluid via the sample collector port 32. When pressurized by the cover 18, the removable cartridge 14 performs blood dilution, red cell lysing, and hydrodynamic focusing for core formation in the present device. Once formed, the core is provided down a flow stream path 50, which passes the flow stream windows 30a and 30b of FIG. 1. The light sources 22a and 22b, and associated optics in the base provide light through and to the core stream via the flow stream windows 30a and 30b. The light detectors 24a and 24b, and associated optics receive scattered and non-scattered light from the core, also via the flow stream windows 30a and 30b, respectively. The controller or processor 40 receives output signals from the detectors 24a and 24b, and differentiates, identifies and counts selected white blood cells that are present in the core stream.

It is contemplated that the removable cartridge 14 may include a fluid control block 48 for helping control the velocity of each of the fluids. In the illustrative example, the fluid control block 48 includes flow sensors for sensing the velocity of the various fluids and reports the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 may have a waste reservoir 52 downstream of the flow stream windows 30a and 30b. The waste reservoir 52 receives and stores the fluid of the flow stream in the removable cartridge 14. When a test is completed, the removable cartridge may be removed and disposed of, often in a container compatible with biological waste.

Figure 3:
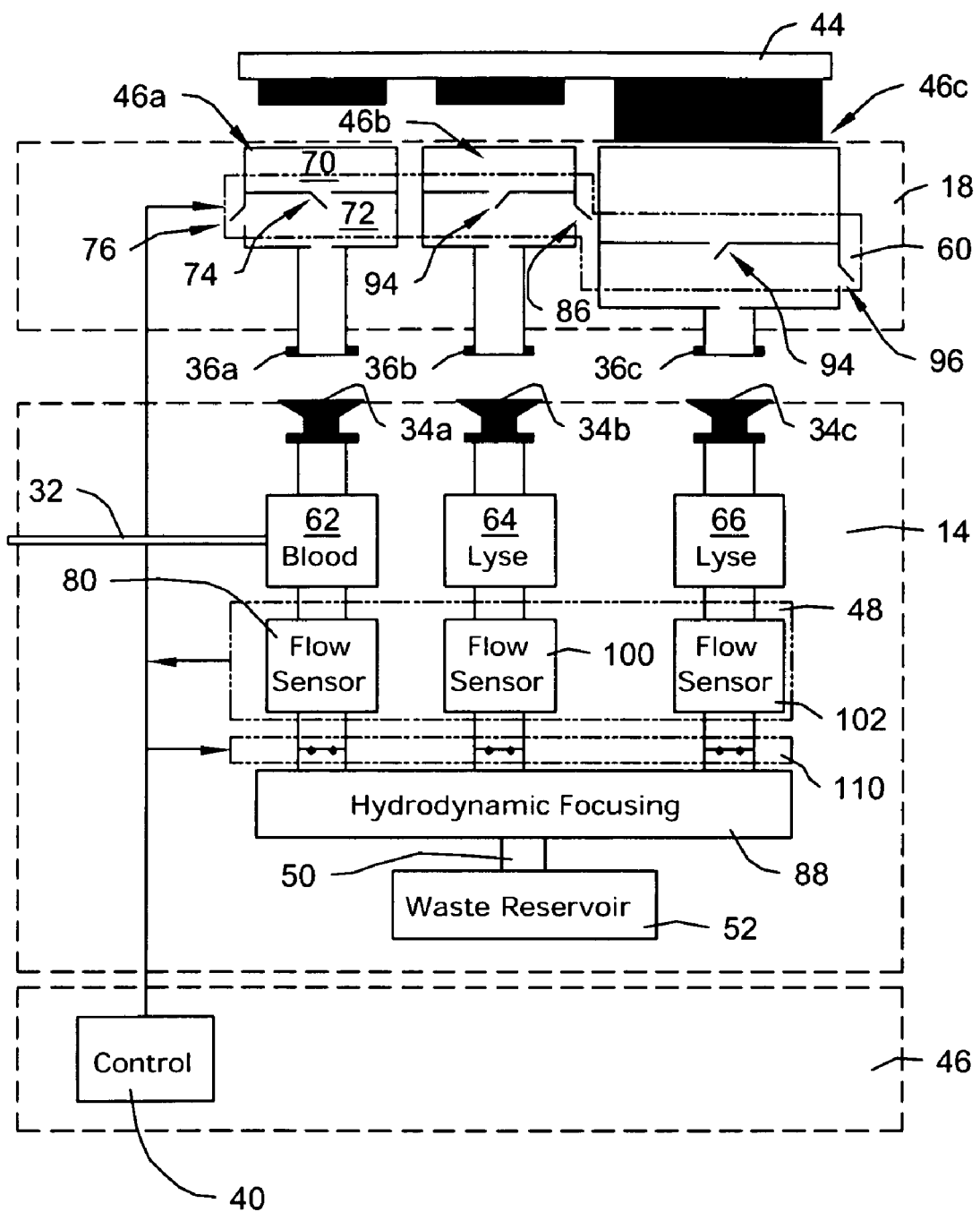
FIG. 3 is a more detailed schematic diagram showing the cytometer of FIG. 2 with the cover not yet depressed.
Figure 4:
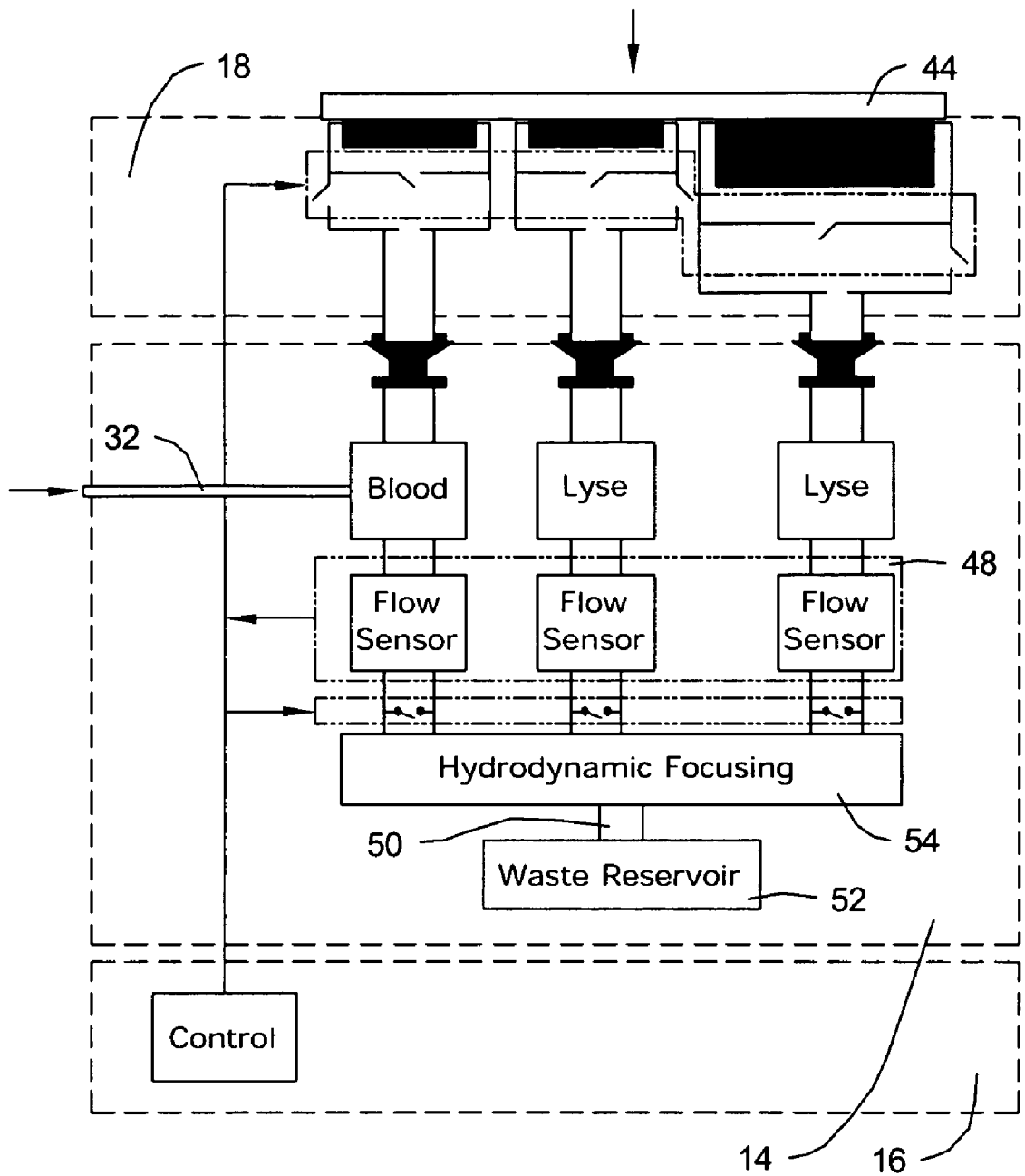
FIG. 4 is a more detailed schematic diagram showing the cytometer of FIG. 2 with the cover depressed.

FIG. 3 is a more detailed schematic diagram showing the cytometer of FIG. 2 with the cover 18 not yet depressed. FIG. 4 is a more detailed schematic diagram showing the cytometer of FIG. 2 with the cover depressed. The cover 18 is shown having a manual pressurizing element 44, pressure-chambers 46a, 46b and 46c, and control microvalves generally shown at 60. The light sources and detectors are not shown in these Figures.

There are three pressure chambers 46a, 46b and 46c, one for each fluid to be pressurized. In the illustrative example, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is may be an array of electrostatically actuated microvalves that are individually addressable and controllable, as described in, for example, co-pending U.S. patent application Ser. No. 09/404,560, entitled "Addressable Valve Arrays for Proportional Pressure or Flow Control", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 may be filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focusing. Each flow sensor 80, 100 and 102 measures the velocity of the corresponding fluid. The flow sensors may be thermal anemometer type flow sensors such as microbridge type flow sensor. Microbridge flow sensors are described in, for example, U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 5,050429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valves 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another illustrative example of the invention, downstream valves 110 are opened by mechanical action when the cover is closed.

Figure 5:
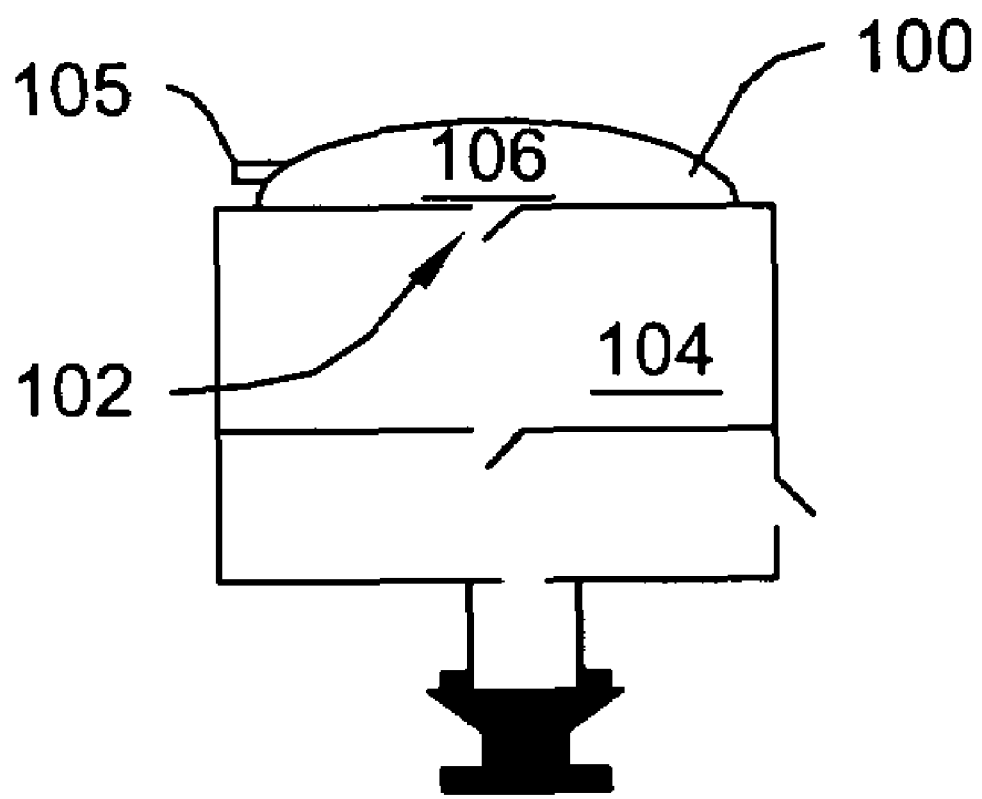
FIG. 5 is a schematic diagram showing an illustrative manual fluid driver having a bulb and check valve.

FIG. 5 is a schematic diagram showing an illustrative manual fluid driver having a bulb 100 and check valve 102. The check valve 102 may be a one way valve that allows air in but not out of the first pressure chamber 104. When the bulb 100 is depressed, the air in the interior 106 of the bulb 100 is forced through the check valve 102 and into the first pressure chamber 104. Another one-way vent valve 105 may be provided that allows air in from the atmosphere but not out of the interior 106 of the bulb 100. Thus, when the bulb is released, the one-way vent valve 105 may allow replacement air to flow into bulb 100.

Rather than using a manually operated fluid driver, it is contemplated that any relatively small pressure source may be used including, for example, an electrostatically actuated meso-pump. One such meso-pump is described in, for example, U.S. Pat. No. 5,836,750 to Cabuz, which is incorporated herein by reference.

Figure 6:
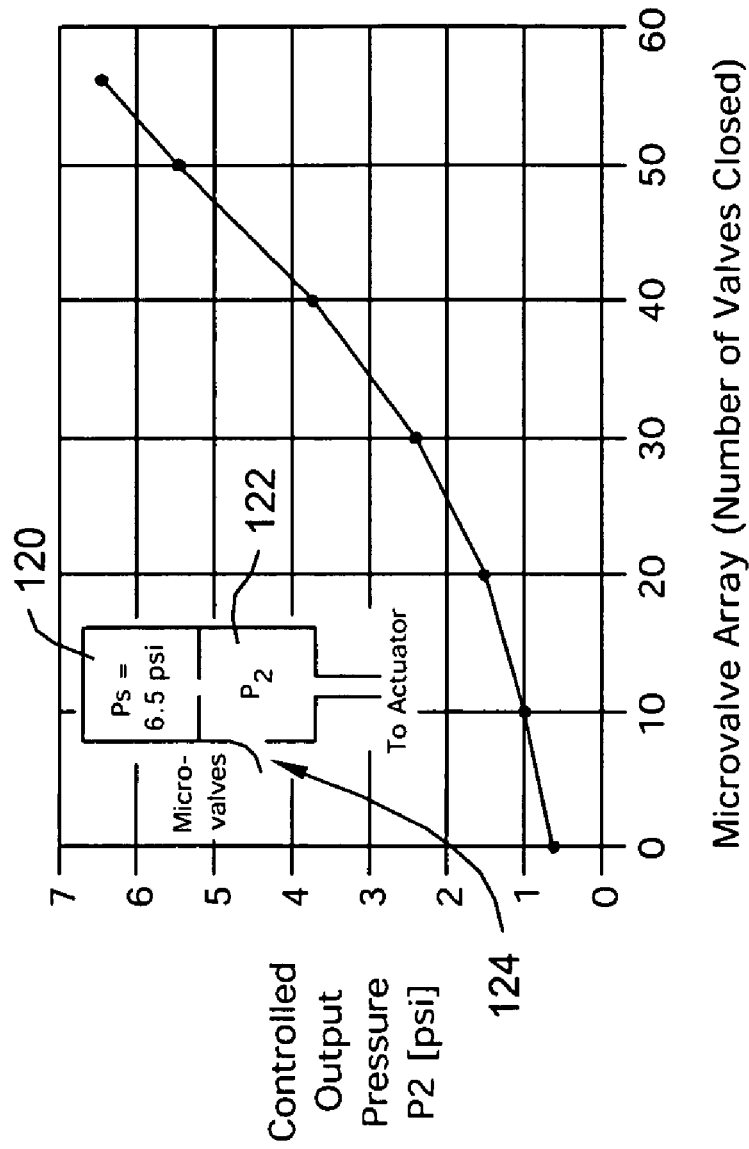
FIG. 6 is a graph showing proportional pressure control of an addressable array of microvalves.

FIG. 6 is a graph showing proportional pressure control produced by an 8×7 addressable array of microvalves. To create the graph shown in FIG. 6, 6.5 psi was applied to a first pressure chamber 120. A small opening was provided to a second pressure chamber 122. The microvalves are shown at 124, and vent the pressure in the second pressure chamber 122. By changing the number of addressable microvalves that are closed, the pressure in the second pressure chamber can be changed and controlled. In the graph shown, the pressure in the second pressure chamber 122 could be changed from about 0.6 psi, when zero of the 8×7 array of microvalves close, to about 6.5 psi, when all of the 8×7 array of microvalves are closed. These low power, micromachined silicon microvalves can be used for controlling pressures up to 10 psi and beyond.

Figure 7:
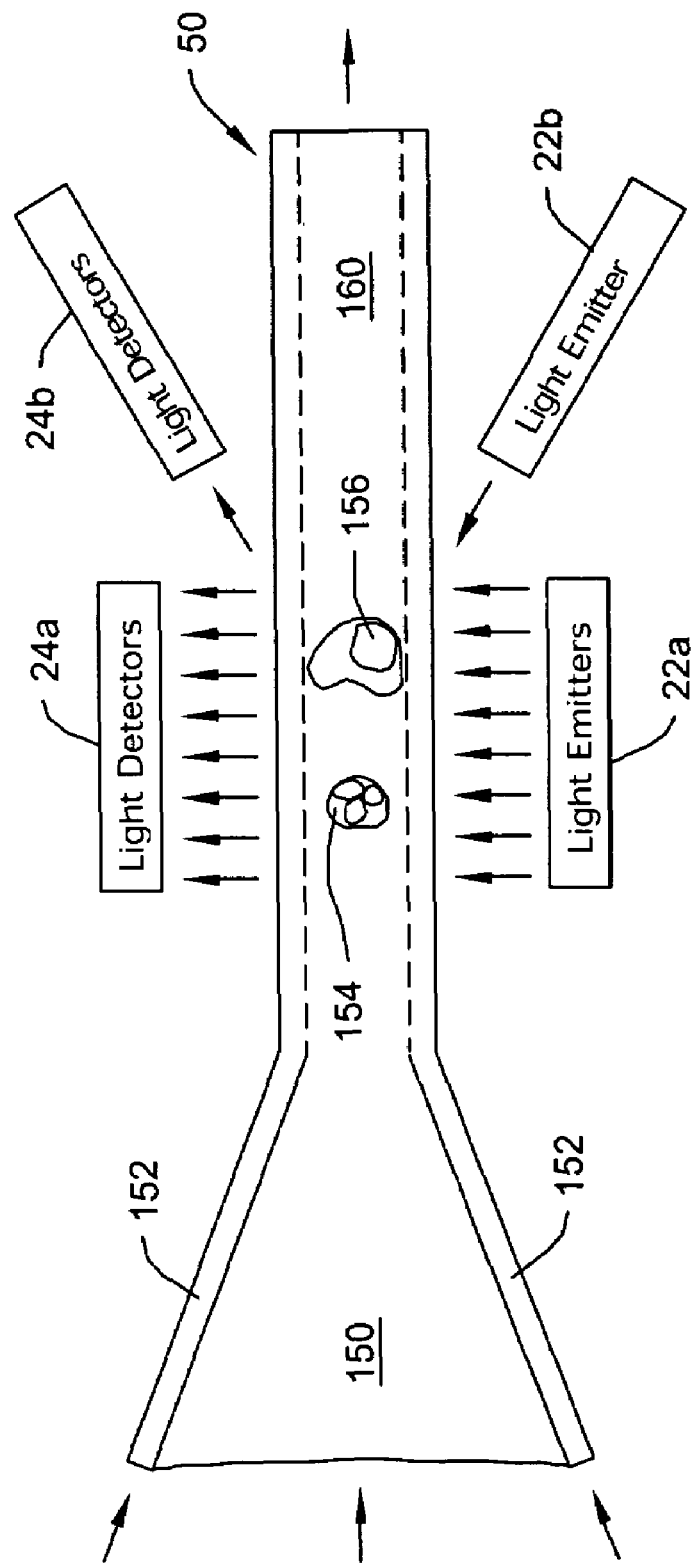
FIG. 7 is a schematic diagram showing the formation of a flow stream by the hydrodynamic focusing block 88 of FIG. 3.

FIG. 7 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. The lysing solution may have a pH lower than that of the red blood cells. This is often referred to as red cell lysing or lyse-on-the-fly. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white blood cells 154 and 156 are in single file. The velocity of the sheath fluid may be about 9 or more times than that of the core stream 160, but any suitable velocities may be used. The velocity of the sheath fluid and core stream 160 may remain sufficiently low, however, to maintain laminar flow in the flow channel.

Light emitters 22a and/or 22b, and associated optics may be provided adjacent one side of the flow stream 50. Light detectors 24a and/or 24b, and associated optics may be provided on another side of the flow stream 50 for receiving the light from the light emitters 22a, and in some cases, light from fluorescing particles via the flow stream 50. The output signals from the light detectors 24a and 24b are provided to controller or processor 40, wherein they are analyzed to identify and/or count selected white blood cells or other particles in the core stream 160.

Figure 8:
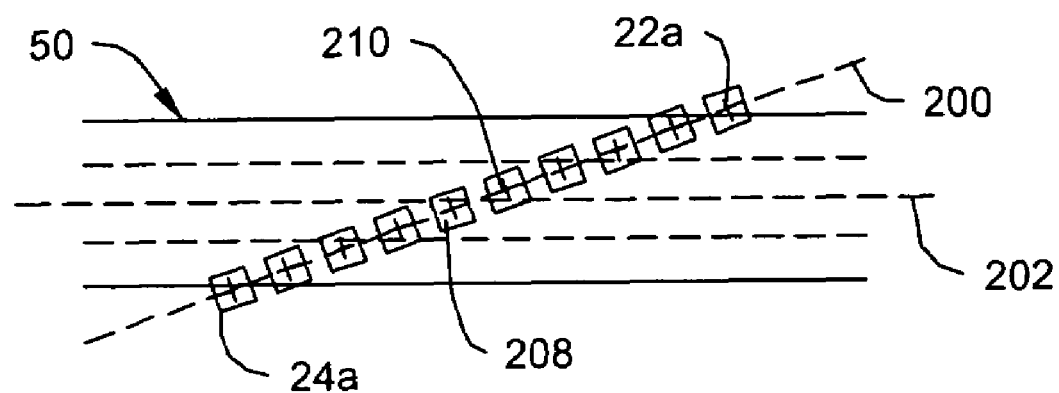
FIG. 8 is a schematic diagram showing an array of light sources and an array of light detectors for analysis of the core stream 160 of FIG. 7.

FIG. 8 is a schematic diagram showing an array 22a of light sources and an array 24a of light detectors for analysis of the core stream 160 via scattering of FIG. 7. The light sources are shown as "+" signs and the detectors are shown at boxes. In the example shown, the array of light sources is provided adjacent one side of the flow stream 50, and the array of light detectors is provided adjacent the opposite side of the flow stream. Each of the light detectors may be aligned with a corresponding one of the light sources. The array of light sources and the array of light detectors are shown arranged along a light source axis 200 that is slightly rotated relative to the axis 202 of the flow stream 50, but this is not required in all embodiments.

The array 22a of light sources may be an array of lasers such as vertical cavity surface emitting lasers (VCSELs) fabricated on a common substrate. Because of their vertical emission, VCSELs are ideally suited for packaging in compact instruments such as a miniaturized portable cytometer. Such cytometer may be wearable on a person's body. In some cases, the VCSELs are "red" VCSELs that operate at wavelengths that are less than the conventional 850 nm, and in some cases in the 670 nm to 780 nm range. Red VCSELs may have a wavelength, power and polarization characteristic that is ideally suited for scatter measurements.

Some prior art cytometer bench models use a single 9 mW edge-emitting laser with a wavelength of 650 nm. The beam is focused to a 10×100 micron elongated shape to cover the uncertainty in particle position due to misalignment and width of the core stream. In contrast, the output power of the red VCSELs of the present invention, operating at 670 nm, is typically around 1 mW for a 10×10 micron emitter and 100-micron spacing. Thus, the total intensity of the light from a linear array of ten red VCSELs may be essentially the same as that of some prior art bench models.

Using a linear array of lasers oriented at an angle with respect to the flow axis 202 offers a number of important advantages over the single light source configuration of the prior art. For example, a linear array of lasers may be used to determining the lateral alignment of the path of the particles in the core steam. One source of uncertainty in the alignment of the particle stream is the width of the core flow, which leads to statistical fluctuations in the particle path position. These fluctuations can be determined from analysis of the detector data, and in some cases can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells pass through several focused spots produced by the linear array of VCSELs. The cells produce a drop in signal in the corresponding in-line reference detectors. The relative strengths of the signals are used by the controller or processor 40 to determine the center of the particle path and a measure of the particle width.

In some cases, the light sources may be sequentially activated. A change in the response of each of the detectors may then be monitored as particles passes between the detector and the activated light source. By determining which of the light sources, when activated, produces the largest change in response at the detector and/or the largest scatter signature, the alignment of the flow stream in the flow channel may be uniquely determined. In some cases, the largest change may correspond to a largest change in the scatter signature. In other cases, and particularly when the particles tend to block the light beam, the largest change may correspond to a largest change in amplitude (e.g. decrease in amplitude) of the detected signal. In yet other cases, the number of particles in the flow stream may be counted, and the light source that produces the largest particle count may be selected. In some cases, and during subsequent measurements, only the light source that produced the largest change in response at the detector, largest scatter signature, and/or the largest particle count is activated.

Figure 10:
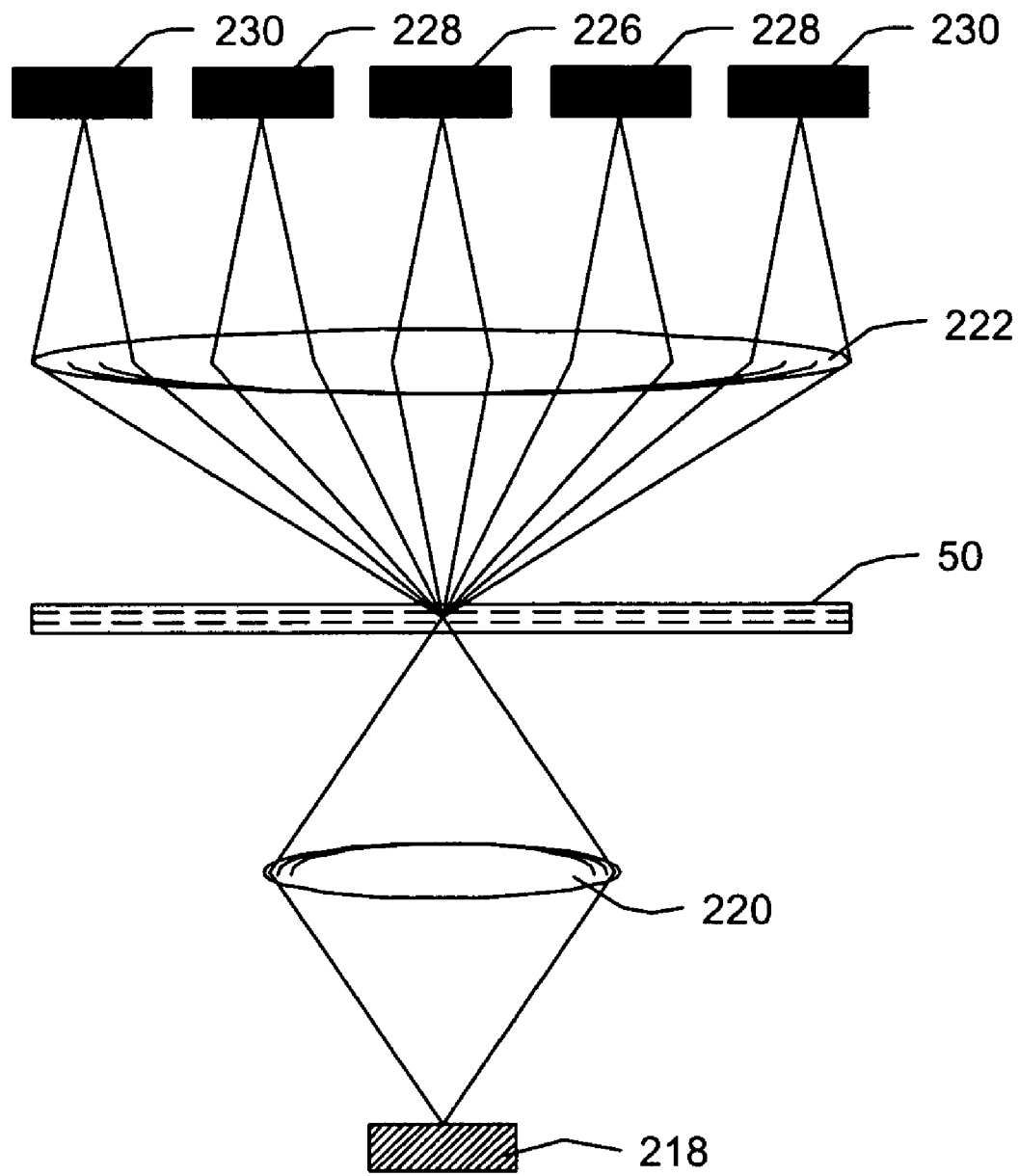
FIG. 10 is a schematic diagram showing an illustrative light source and detector pair of FIG. 8.

In some cases, an actuator or the like (not explicitly shown) may be used to move the replaceable cartridge 14 relative to the housing 12, and/or to move a lens such as lens 220 of FIG. 10 to steer the beam from the light source, so that the flow stream is aligned with a particular light source.

In other cases, only a single light source may be provided rather than an array of light sources. An actuator or the like (not explicitly shown) may then be used to move the replaceable cartridge 14 relative to the housing 12 and thus relative to the single light source, and/or to move a lens such as lens 220 of FIG. 10 to steer the beam from the light source, until the flow stream is properly aligned with the light beam produced by the light source. This may reduce the number of light sources that are required.

Figure 9:
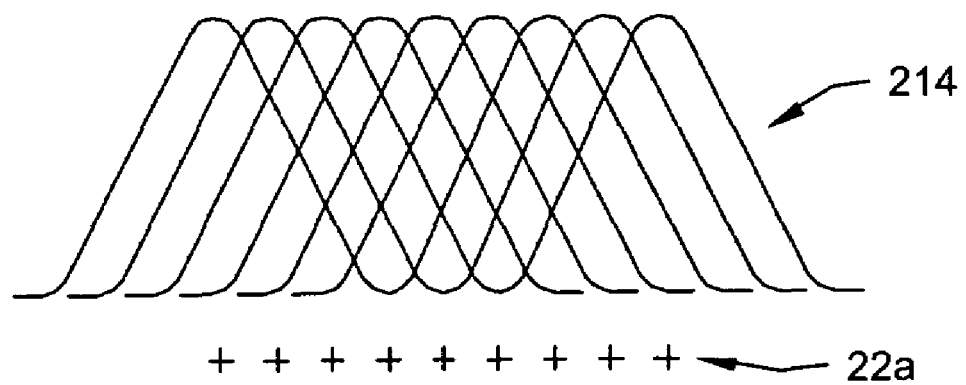
FIG. 9 is a graph showing the light intensity produced along the light source axis of FIG. 8.

In some embodiments, and for determining particle path and size, the lasers 22a may be focused to a series of Gaussian spots 214 (intensity on the order of 1000 W/cm$^2$) in the plane of the core flow. The spots 214 may be about the same size as a white blood cell (10-12 um). Illustrative Gaussian spots 214 are shown in FIG. 9. Arrays 24a of detectors and their focusing optics are provided on the opposite side of the fluid stream 50. Lenses with fairly large F-numbers are used to provide a working space of several hundred microns for the cytometer section of the removable cartridge.

Another advantage of using a linear array 22a of lasers rather than a single laser configuration is that the velocity of each cell may be determined using the linear array 22a. However, as further described below, other methods are contemplated for determining the velocity of the particles in the flow stream. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as microbubbles can be introduced to disturb the flow or core formation.

To determine the velocity of each cell, the system may measure the time required for each cell to pass between two adjacent or successive spots. For example, and with reference to FIG. 8, a cell may pass detector 208 and then detector 210. By measuring the time required for the cell to travel from detector 208 to detector 210, and by knowing the distance from detector 208 to detector 210, the controller or processor 40 can calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array 22a of lasers rather than a single laser configuration is that a relatively constant light illumination may be provided across the flow channel. As noted above, however, this is not required in all embodiments. This is accomplished by overlapping the Gaussian beams 214 from adjacent VCSELs 22a, as shown in FIG. 9. In prior art single laser systems, the light illumination across the flow channel typically varies across the channel. Thus, if a particle is not in the center of the flow channel, the accuracy of subsequent measurements may be diminished.

To perform the above described measurements, each detector 24a in FIG. 8 may be a single in-line detector. To measure FALS and SALS scatter, however, each detector 24a may further include two annular detectors disposed around the in-line detector, as shown in FIG. 10. Referring to FIG. 10, a VCSEL 218 is shown providing light in an upward direction. The light is provided through a lens 220, which focuses the light to a Gaussian spot in the plane of the core flow. Lens 220 may be a microlens or the like, which is either separate from or integrated with the VCSEL 218. The light passes through the core flow, and is received by another lens 222, such as a diffractive optical element. Lens 222 provides the light to in-line detector 226 and annular detectors 228 and 230. The in-line detector 226 detects the light that is not significantly scattered by the particles in the core stream. Annular detector 228 detects the forward scatter (FALS) light, and annular detector 230 detects the small angle scatter (SALS) light.

Figure 11:
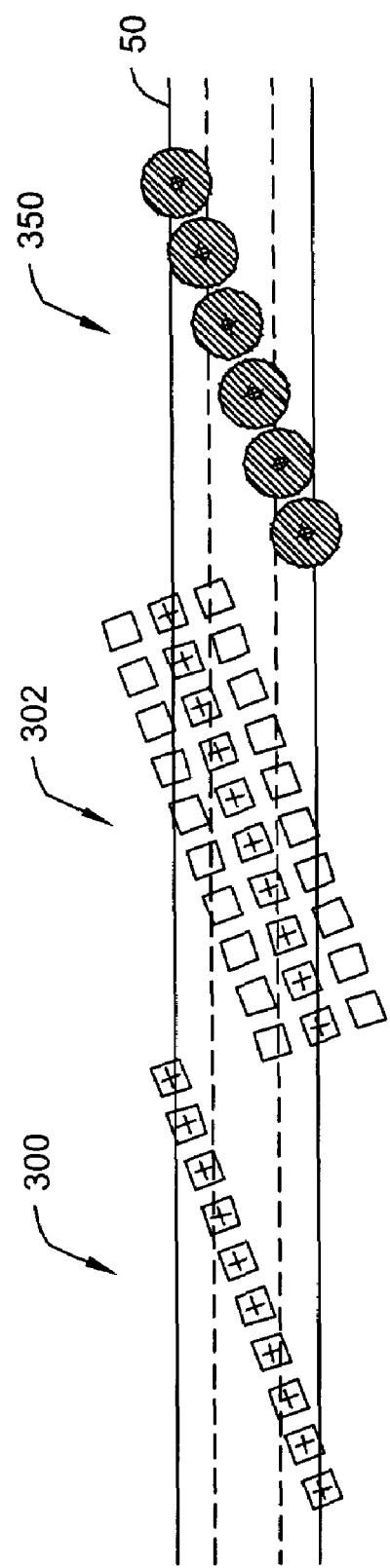
FIG. 11 is a schematic diagram showing three separate arrays of light sources and detectors, each positioned along a different light source axis that is slightly rotated relative to the central flow axis of the flow stream of FIG. 7.

FIG. 11 shows another illustrative example of the present invention that includes three separate arrays of light sources and light detectors. Each array of light sources and light detectors are positioned along a different light source axis that is slightly rotated relative to the central flow axis of the flow stream. By using three arrays, the optics associated with each array may be optimized for a particular application or function. For detecting small angle scattering (SALS), laser light that is well-focused on the plane of the core flow is desirable. For detecting forward scattering (FALS), collimated light is desirable.

Referring specifically to FIG. 11, a first array of light sources and light detectors is shown at 300. The light sources and light detectors are arranged in a linear array along a first light source axis. The first light source axis is rotated relative to the flow axis of the flow stream. The light sources and light detectors may be similar to that described above with respect to FIG. 8, and may be used to measure, for example, the lateral alignment of the cells in the flow stream—which in some cases may be used to select a particular light source for use during subsequent measurements, as well as to help determine the particle size, and the velocity of the particles.

Figure 12:
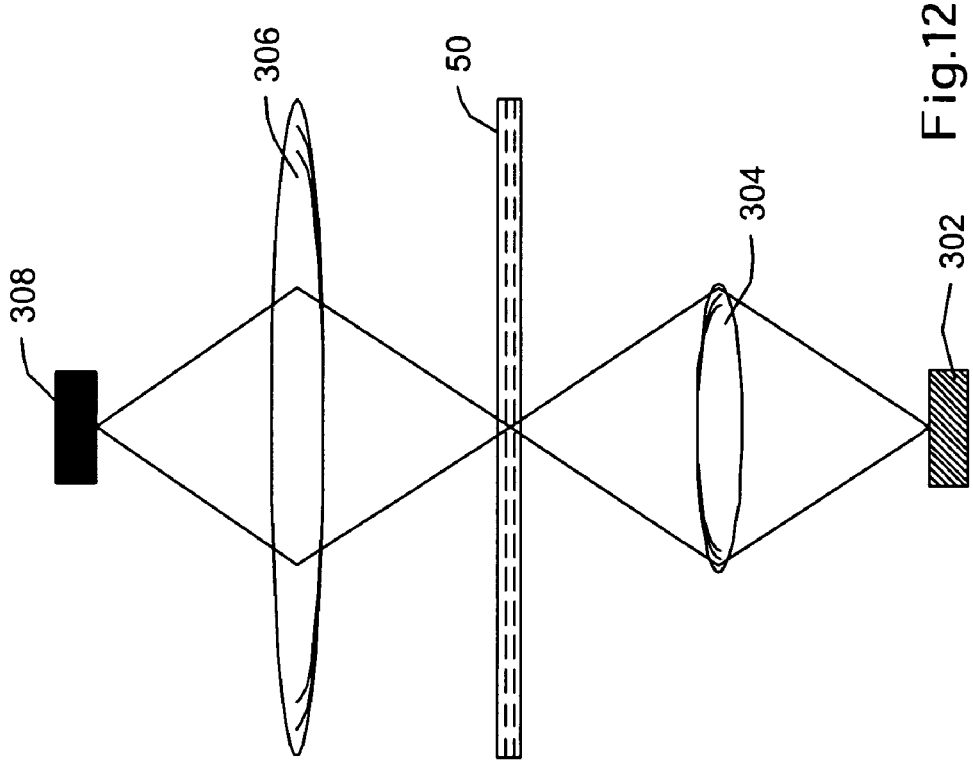
FIG. 12 is a schematic diagram showing an illustrative light source and detector pair of the first array shown in FIG. 11.

FIG. 12 is a schematic diagram showing an illustrative light source and detector pair of the first array 300 shown in FIG. 11. A VCSEL 302 is shown providing light in an upward direction. The light is provided through a lens 304, which focuses the light to a Gaussian spot in the plane of the core flow. The light passes through the core flow, and is received by another lens 306. Lens 306 provides the light to in-line detector 308. The in-line detector 308 detects the light that is not significantly scattered by the particles in the core stream.

A second array of light sources and light detectors is shown at 310. The light sources are arranged in, for example, a linear array along a second light source axis that is rotated relative to the flow axis of the flow stream. The light detectors include three linear arrays of light detectors. One array of light detectors is positioned in line with the linear array of light sources. The other two linear arrays of light detectors are placed on either side of the in-line array of light detectors, and are used for measuring the small angle scattering (SALS) produced by selected particles in the flow stream.

Figure 13:
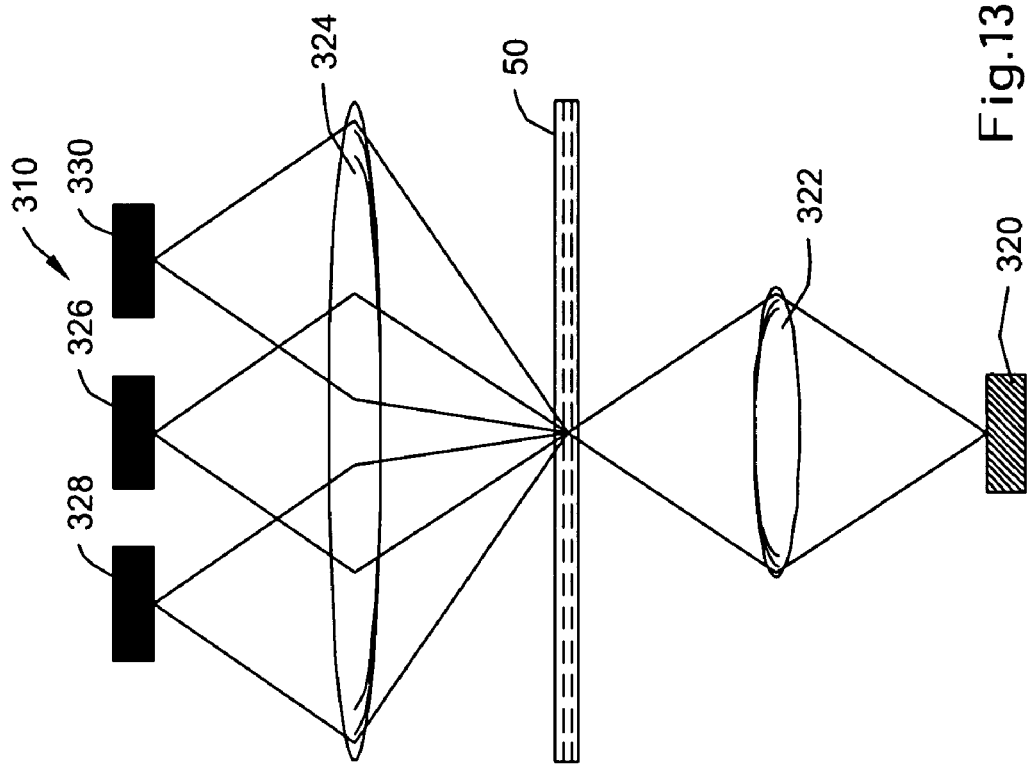
FIG. 13 is a schematic diagram showing an illustrative light source and detector pair of the second array shown in FIG. 11.

FIG. 13 is a schematic diagram showing an illustrative light source and corresponding detectors of the second array shown in FIG. 11. A VCSEL 320 is shown providing light in an upward direction. The light is provided through a lens 322, which focuses the light to a Gaussian spot in the plane of the core flow. The light passes through the core flow, and is received by another lens 324, such as a diffractive optical element (DOE) 324. Lens 324 provides the light to the in-line detector 326 and the two corresponding light detectors 328 and 330 placed on either side of the in-line light detector 326.

The in-line detector 326 may be used to detect the light that is not significantly scattered by the particles in the core stream. Thus, the in-line linear array of light detectors of the second array 302 may be used to provide the same measurements as the in-line array of detectors of the first array 300. The measurements of both in-line arrays of detectors may be compared or combined to provide a more accurate result. Alternatively, or in addition, the in-line detectors of the second array 302 may be used as a redundant set of detectors to improve the reliability of the cytometer.

It is contemplated that the in-line detectors of the second array 302 may also be used in conjunction with the in-line detectors of the first array 300 to more accurately determine the time-of-flight or velocity of the particles in the flow stream. The measurement may be more accurate because the distance between detectors may be greater. Also, if only a selected light source is used during subsequent measurements rather than all of the light sources in the light source array, the velocity of the particles in the flow stream may be determined. As indicated above, by knowing the velocity of the particles, small variations in the flow rate caused by the fluid driver can be minimized or removed by the controller, and the size of the particles may more readily be determined.

Light detectors 328 and 330 of FIG. 13 are used to measure the small angle scattering (SALS) produced by selected particles in the flow stream. The light detectors 328 and 330 may therefore be spaced sufficiently from the in-line detector 326 to intercept the small angle scattering (SALS) produced by selected particles in the flow stream.

Referring back to FIG. 11, a third array of light sources and light detectors 350 may be provided to measure the forward angle scattering (FALS) produced by selected particles in the flow stream. The light sources are arranged in a linear array along a third light source axis that is rotated relative to the flow axis of the flow stream. Each light source may have a corresponding light detector, and each light detector may have an annular shaped with a non-sensitive region or a separate in-line detector in the middle. The annular shaped light detectors may be sized to intercept and detect the forward angle scattering (FALS) produced by selected particles in the flow stream.

Figure 14:
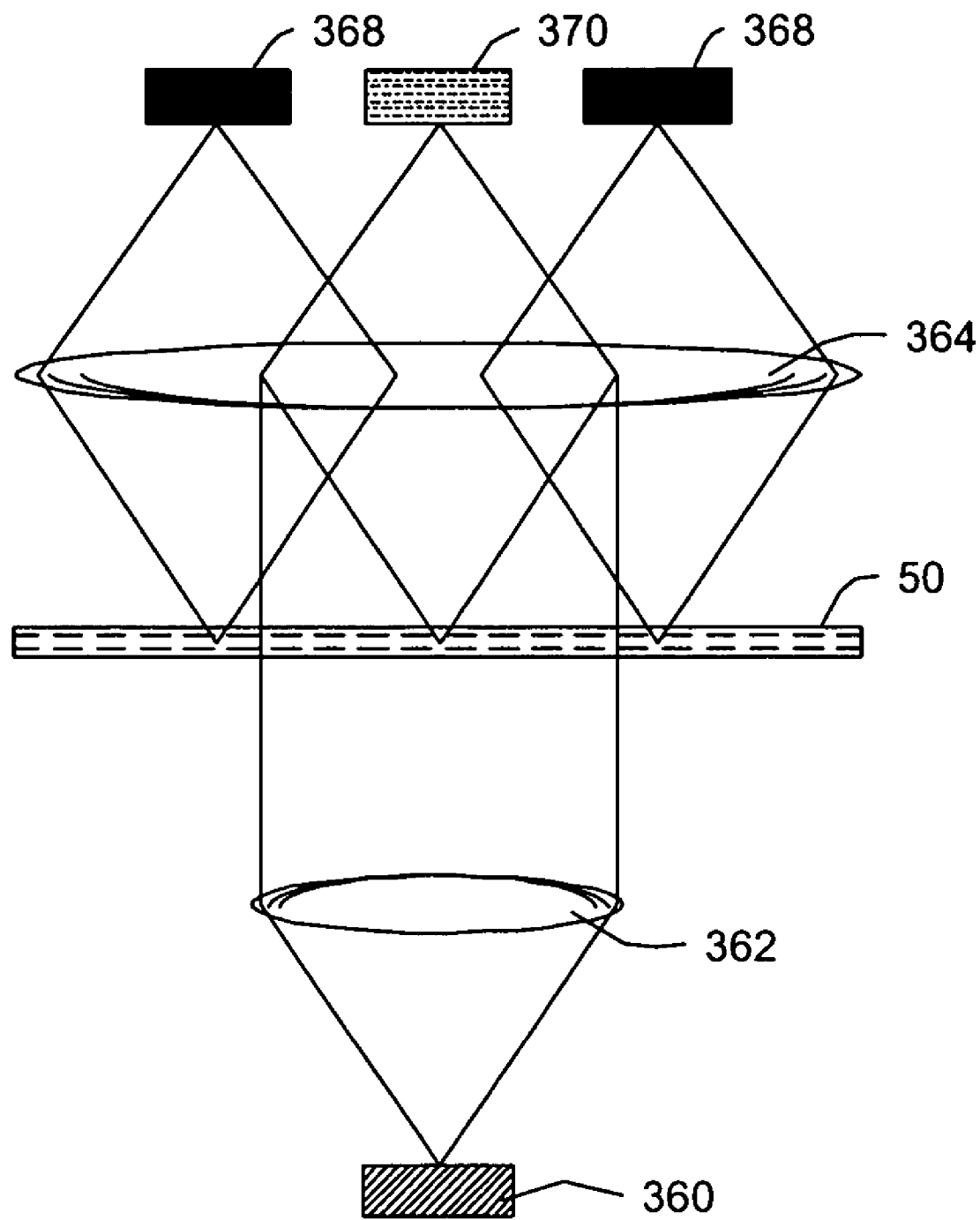
FIG. 14 is a schematic diagram showing an illustrative light source and detector pair of the third array shown in FIG. 11.

FIG. 14 is a schematic diagram showing an illustrative light source and detector pair of the third array of light sources and light detectors 350 shown in FIG. 11. A VCSEL 360 is shown providing light in an upward direction. The light is provided through a lens 362 such as a collimating lens, which provides substantially collimated light to the core flow. As indicated above, collimated light is desirable for detecting forward scattering (FALS) light. The light passes through the core flow, and is received by another lens 364. Lens 364 provides the received light to the annular shaped detector 368.

The annular shaped detector 368 may be sized to intercept and detect the forward angle scattering (FALS) produced by selected particles in the flow stream. A non-sensitive region or a separate in-line detector 370 may be provided in the middle of the annular shaped detector 368. If a separate in-line detector 370 is provided, it can be used to provide the same measurement as the in-line detectors of the first array 300 and/or second array 302. When so provided, the measurements from all three in-line arrays of detectors of first array 300, second array 302 and third array 350 may be compared or combined to provide an even more accurate result. The in-line detectors of the third array 302 may also be used as another level or redundancy to improve the reliability of the cytometer.

It is contemplated that the in-line detectors of the third array 350 may also be used in conjunction with the in-line detectors if the first array 300 and/or second array 302 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller, and the size of the particles may more readily be determined.

By using three separate arrays of light sources and detectors, the optics associated with each array can be optimized for the desired application. As can be seen, the optics associated with the first array 300 may be designed to provide well-focused laser light on the plane of the core flow. This helps provide resolution to the alignment, size and particle velocity measurements performed by the first array 300. Likewise, the optics associated with the second array 302 may be designed to provide well-focused laser light on the plane of the core flow. Well focused light is desirable when measuring the small angle scattering (SALS) produced by selected particles in the flow stream. Finally, the optics associated with the third array 350 may be designed to provide collimated light to the core flow. As indicated above, collimated light is desirable when measuring forward angle scattering (FALS) produced by selected particles in the flow stream.

Figure 15:
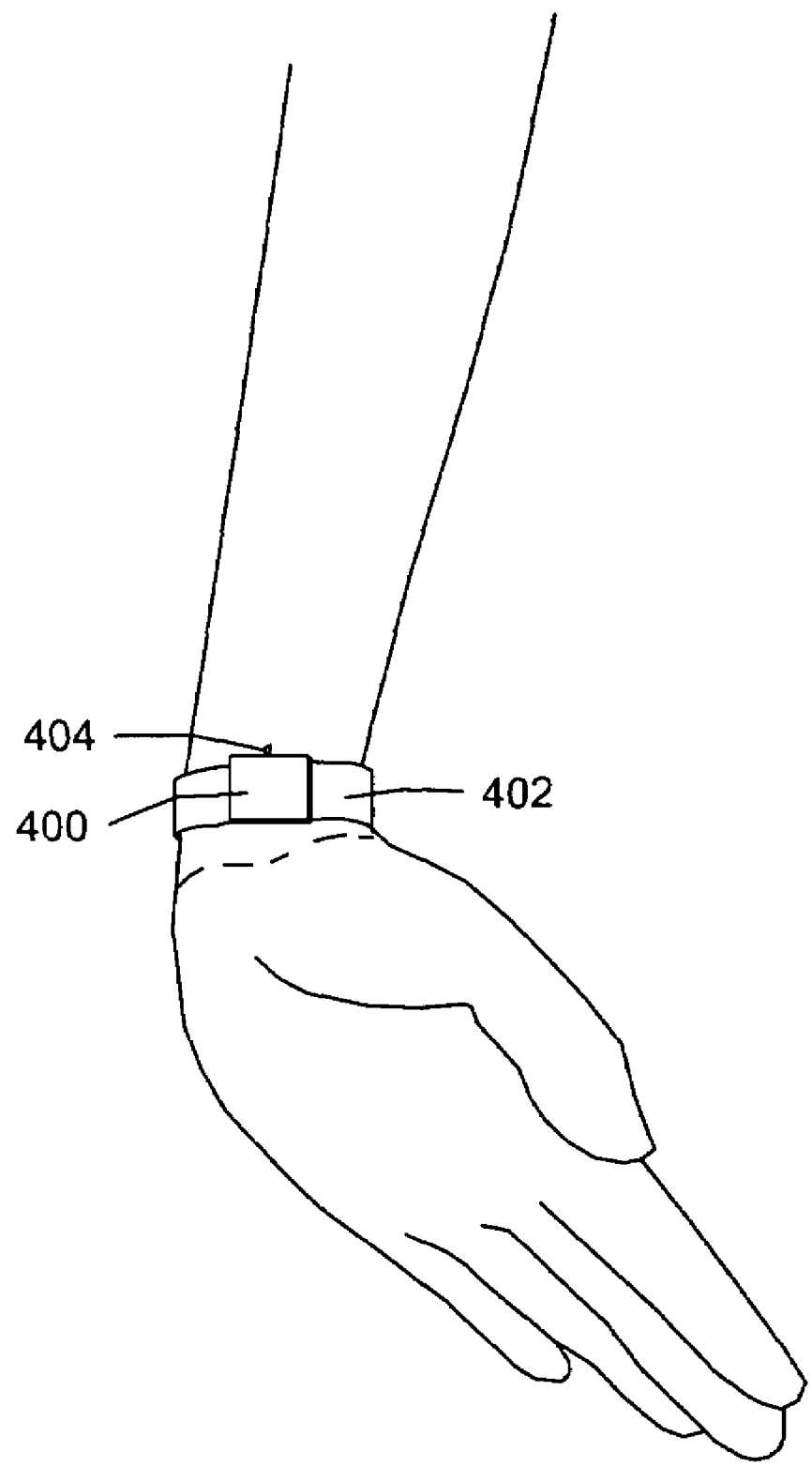
FIG. 15 is a perspective view of an illustrative example of the miniaturized portable cytometer adapted to be worn around the wrist.

FIG. 15 is a perspective view of an illustrative example of the miniaturized portable cytometer of the present invention adapted to be worn around the wrist. This cytometer 400 may be similar to that shown in FIG. 1. A band 402 secures cytometer 400 to the wrist of a user.

As indicated above, the user may obtain a removable cartridge and provide a blood sample to the sample collector port 32 (see FIG. 1) of the removable cartridge. The blood sample may be collected by, for example, a finger prick. The user may then insert the removable cartridge into the housing, and manually pressurize the system. The miniaturized portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 404 or the like may be inserted into a vein of the user and attached to the sample collector port 32. This may allow the system to automatically collect a blood sample from the user whenever a reading is desired. Alternatively, it is contemplated that the miniaturized portable cytometer may be implanted in the user, with the sample collector port 32 connected to a suitable blood supply.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. An optical detection system for analyzing predetermined characteristics of a flow stream, the flow stream having a width dimension perpendicular to the direction of flow and the flow stream having a central axis extending in the direction of the flow stream, the optical detection system comprising:

two or more light sources, each for providing a light beam primarily through a different part of the flow stream in the width dimension, wherein the light beams of the two or more light sources are intentionally offset from one another to pass primarily through the flow stream at different distances from the central axis of the flow stream in the width dimension;

light receiving means for receiving the light beam from a selected light source, and for providing at least one signal in response thereto; and processing means for receiving the at least one signal from the light receiving means and for using the at least one signal for analyzing the predetermined characteristics of the flow stream.

2. The optical detection system of claim 1 wherein at least some of the light beams passing through the different parts of the flow stream at least partially overlap an adjacent light beam.

3. The optical detection system of claim 1 wherein the at least one signal includes a scattering signature.

4. The optical detection system of claim 3 wherein the selected light source is the light source that produces a scattering signature with the greatest amplitude.

5. The optical detection system of claim 3 wherein the selected light source is the light source that produces a smallest amplitude signal detected at the light receiving means.

6. The optical detection system of claim 1 wherein at least one of the predetermined characteristics of the flow stream includes a count of cells in the flow stream, and wherein the selected light source is the light source that produces a largest cell count.

7. The optical detection system of claim 1 wherein the two or more light sources are Vertical Cavity Surface Emitting Lasers (VCSELs).

8. The optical detection system of claim 1 wherein the light receiving means includes at least one photodetector.

9. The optical detection system of claim 1, wherein each of the two or more light sources have a corresponding lens.

10. A method for analyzing predetermined characteristics of a flow stream, the flow stream having a width dimension perpendicular to the direction of flow and having a central axis along the direction of flow, the method comprising the steps of:

providing two or more light sources, each for providing a light beam primarily through a different part of the flow stream in the width dimension, wherein the light beams of the two or more light sources are intentionally offset from one another to pass primarily through the flow stream at different distances from the central axis of the flow stream in the width dimension;

selecting one of the two or more light sources;

activating the selected light source, while deactivating the other light sources;

receiving the light from the selected light source, and providing at least one signal in response thereto; and analyzing the predetermined characteristics of the flow stream using the at least one signal.

11. The method of claim 10 wherein at least some of the light beams passing through different parts of the flow stream at least partially overlap an adjacent light beam.

12. The method of claim 10 wherein the at least one signal includes a scattering signature.

13. The method of claim 12 wherein the selected light source is the light source that produces a scattering signature with the greatest amplitude.

14. The method of claim 10 wherein the two or more light sources are Vertical Cavity Surface Emitting Lasers (VCSELs).

15. A method for determining the alignment of one or more particles in a flow stream relative to a width dimension of the flow stream, the method comprising:

activating and deactivating in sequence each of two or more light sources, each light source providing a light beam, wherein the light beams of the two or more light sources are intentionally offset from one another in the width dimension to pass primarily through different parts of the flow stream in the width dimension;

monitoring an output response of at least one detector that receives the light from the two or more light sources;

detecting a change in the response of the at least one detector when a particle passes between the detector and a corresponding activated light source;

determining which of the light sources, when activated, produces the largest change in the response of the at least one detector;

selecting the light source that produces the largest change in the response of the at least one detector; and activating the selected light source, while deactivating the other light sources.

16. The method of claim 15 wherein at least some of the light beams passing through different parts of the flow stream at least partially overlap an adjacent light beam.

17. The method of claim 15 wherein the response of the at least one detector includes a scattering signature.

18. The method of claim 17 wherein the selected light source is the light source that produces a scattering signature with the greatest amplitude.

19. The method of claim 15 wherein the selected light source is the light source that produces the smallest amplitude signal when a particle passes between the detector and a corresponding light source.

20. The method of claim 15 wherein the selected light source is the light source that produces a largest particle count.

21. The method of claim 15 wherein the two or more light sources are Vertical Cavity Surface Emitting Lasers (VCSELs).

22. A method for determining the alignment of one or more particles in a flow stream relative to a width dimension of the flow stream, the method comprising:

activating and deactivating in sequence each of two or more light sources, each light source providing a light beam, wherein the light beams of the two or more light sources are intentionally offset from one another in the width dimension to pass primarily through different parts of the flow stream in the width dimension;

monitoring an output response of at least one detector that receives the light from the two or more light sources;

detecting a change in the response of the at least one detector when a particle passes between the detector and a corresponding activated light source;

determining which of the light sources, when activated, produces a signal with a desired characteristic when a particle passes between the detector and a corresponding light source;

selecting the light source that produces the signal with the desired characteristic in the response of the at least one detector; and activating the selected light source, while deactivating the other light sources.

* * * * *